United States Patent [19]

Noakes et al.

[11] Patent Number: 4,829,996
[45] Date of Patent: May 16, 1989

[54] APPARATUS FOR PRODUCING A SPRAY OF DROPLETS OF A LIQUID

[75] Inventors: Timothy J. Noakes, Midhurst; Ian D. Pavey, Southampton; Douglas Bray, Macclesfield; Raymond C. Rowe, Congleton, all of England

[73] Assignee: Imperial Chemical Industries PLC, London, England

[21] Appl. No.: 17,416

[22] Filed: Feb. 24, 1987

[30] Foreign Application Priority Data

Feb. 21, 1986 [GB] United Kingdom ............... 8604328

[51] Int. Cl.⁴ .......................................... A61M 11/00
[52] U.S. Cl. ................... 128/200.14; 239/706
[58] Field of Search ............ 128/200.14, 200.18, 128/200.21, 200.15, 200.16, 200.17; 239/705, 706, 707, 696, 697, 698, 708; 361/227, 228

[56] References Cited

U.S. PATENT DOCUMENTS

| | | | |
|---|---|---|---|
| 398,327 | 2/1889 | DeVars | 128/200.14 |
| 1,958,406 | 5/1934 | Darrah | 361/228 |
| 2,803,248 | 8/1957 | Deuser | 128/200.14 |
| 3,232,292 | 1/1966 | Schaeffer | 128/200.14 |
| 3,698,635 | 10/1972 | Sickles | 239/706 |
| 3,941,312 | 3/1976 | Ohno et al. | 239/696 |
| 4,275,846 | 6/1981 | Coffee | 361/228 |

FOREIGN PATENT DOCUMENTS

| | | | |
|---|---|---|---|
| 239505 | 3/1969 | U.S.S.R. | 128/200.14 |
| 1061822 | 12/1983 | U.S.S.R. | 128/200.14 |
| 2018627 | 11/1979 | United Kingdom . | |
| 1569707 | 6/1980 | United Kingdom . | |

Primary Examiner—Edward M. Coven
Assistant Examiner—John P. Lacyk
Attorney, Agent, or Firm—Cushman, Darby & Cushman

[57] ABSTRACT

Apparatus, for example an inhaler, is disclosed in which a spray is formed electrostatically from an outlet 6 to achieve uniform droplet size. The spray is then discharged for its intended use—in the example inhaling. The spray is discharged completely by corona produced by a sharp discharge electrode 16 which is charged to a polarity opposite that of the liquid. In order to prevent the corona from spoiling the formation of the spray itself, the liquid of the outlet 6 is protected by a neutral shield electrode 8. The spray issues through a hole 14 in the shield electrode. The hole is sufficiently small to prevent corona getting through, yet sufficiently large to allow the spray through.

12 Claims, 3 Drawing Sheets

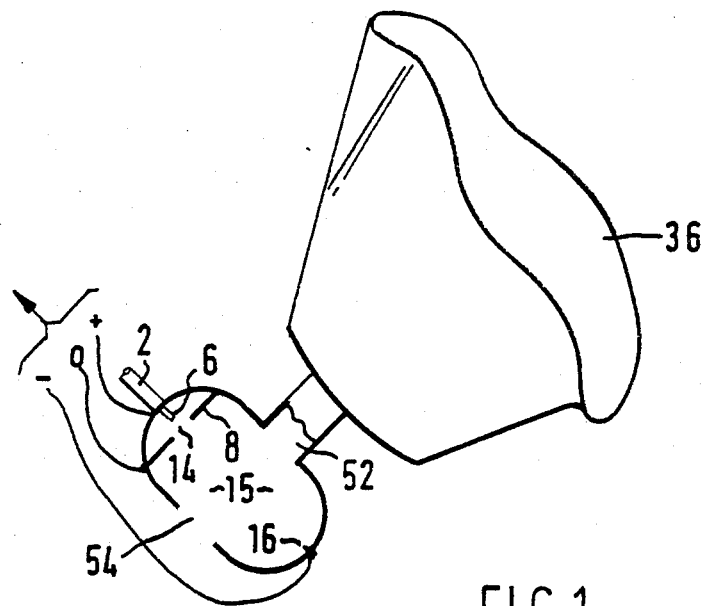
FIG.1
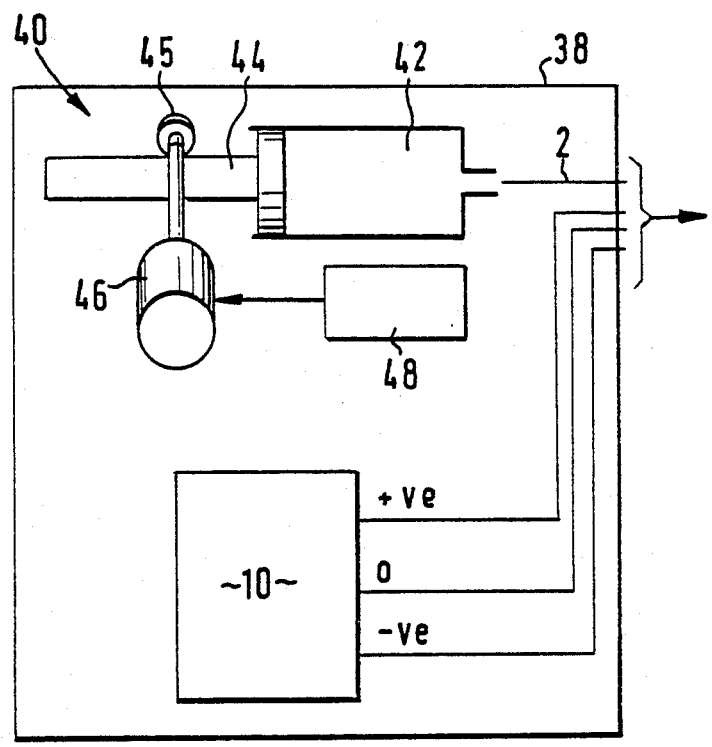

APPARATUS FOR PRODUCING A SPRAY OF DROPLETS OF A LIQUID

FIELD OF THE INVENTION

This invention relates to apparatus for producing a spray of droplets of a liquid.

BACKGROUND OF THE INVENTION

Electrostatic spraying apparatus is described in British patent specification No. 1,569,707, which apparatus comprises a spray head having a conducting or semiconducting surface; means for electrically charging the sprayhead surface to a potential of the order of 1–20 kilovolts; means for delivering spray liquid to the surface; a field-intensifying electrode mounted adjacent to the surface; and means for connecting the field-intensifying electrode to earth, the electrode being so sited relative to the surface that when the surface is charged, the electrostatic field thereat causes liquid thereon to atomise without substantial corona discharge to form electrically charged particles which are projected past the electrode.

In use of such apparatus, as the liquid leaves the surface, it is or becomes charged due to the voltage applied to the surface. The charge produces a repulsive force within the liquid, which overcomes the surface tension thereof causing the liquid to form into one or more cones, sometimes called Taylor cones, dependent on the configuration of the surface. A ligament of liquid is repelled from the tip of the or each cone. The ligament then breaks up into droplets.

The size of the droplets in the spray is distributed over a narrow range compared to other sprayers. The size of the droplets which is obtained depends on the resistivity and the viscosity of the liquid to be sprayed, on the electrical field strength at the spray head, and on the flow rate of the liquid through the spray head. The presence of the field-intensifying electrode adjacent the surface defines the electric field largely independent of the distance of the sprayhead from the target. Therefore the droplet size is largely independent of the distance from the target and can be defined by adjusting the resistivity and the viscosity of the liquid and the voltage applied to the spray head.

The production of a spray of droplets having a narrow size range can be very useful. For example the behaviour of the droplets will be more uniform if the range of sizes is narrow. There are, however, applications when the fact that the droplets are charged is unwanted. British patent specification No. 2,018,627B describes a system for producing a spray which is at least partially discharged. To do this an earthed spike is introduced near the sprayhead. In use an ionic discharge is induced from the spike which discharges the spray at least partially.

A particular application in which it would be useful to produce a non-charged spray of droplets having a narrow distribution of size, is in inhalers to administer drugs to a patient, for example for the treatment of asthma, bronchitis and emphysema. Owing to the fine tubular structure in the lungs the depth to which a particular droplet will penetrate the lungs depends on the size of the droplets. Droplets of the order of 5 microns will reach only the upper respiratory tract, which is quite satisfactory for the treatment of asthma, but for the treatment of emphysema, it is necessary for the droplets to reach the alveoli in the lower respiratory tract, and for this purpose, droplets in the range 0.5 to 2 microns are required. Current state of the art aerosol inhalers produce a wide spectrum of droplet sizes extending up to 37 microns. Current state of the art nebulizers will produce droplets of the required small size, but only in conjunction with droplets of larger sizes, so that with current nebulizers, only a proportion of an anti emphysema drug will reach the required site of action in the alveoli.

Naturally, it is desired that the spray produced be completely discharged for such an application. Charged spray would deposit in the mouth or throat, which would be unpleasant, and would not be inhaled.

In practice, we found it difficult to discharge all of the droplets produced. It was possible, using an earthed needle to discharge a large part of the spray. However, when it was attempted to discharge all the droplets, the ionic discharge (or corona) from the needle reached the cone. This discharged the cone itself which depleted or destroyed the formation of a ligament and thus of a spray.

SUMMARY OF THE INVENTION

This problem is overcome in apparatus for producing a spray of droplets of a liquid, in accordance with the invention, which apparatus comprises: a spraying edge; a shield electrode spaced from the spraying edge and having an orifice through which liquid sprayed from the edge can issue; means for producing a charge to a high potential of one polarity relative to the shield electrode in liquid at the spraying edge, to define an electric field between the edge and the shield electrode sufficient to cause the liquid to issue from the edge as at least one cone from which electrostatic forces repel through the orifice a ligament which breaks up into a spray of charged droplets; a sharp discharge electrode; means for charging the discharge electrode to a high potential of the other polarity relative to the shield electrode, such as to produce a corona to discharge the spray, the shield electrode being of sufficient overall dimensions and having a sufficiently small orifice to shield the edge and the cone of liquid from the corona.

As an example, the spraying edge may be connected to a positive output of a high voltage supply, the shield electrode to earth and the discharge electrode to a negative output. In one alternative, the spraying edge may be connected to a positive high voltage output of the supply, the discharge electrode to a lower voltage output and the shield electrode to an intermediate voltage output.

To have the desired shielding effect, the orifice in the shield electrode must be quite small. We found it surprising that the spray did not merely deposit on the shield. Indeed it will if the orifice is too small. We found it is possible to choose an orifice size which is large enough to allow the spray of droplets through without substantial deposition on the shield electrode, whilst at the same time is small enough to prevent the corona reaching the cone of liquid at the spraying edge.

The shield electrode may be constrained to earth potential or may perhaps float.

The spray itself does not present sufficient space charge to induce an ionic discharge (corona), so because the shield electrode isolates the discharge electrode from the spraying edge, an ionic discharge cannot be induced if the discharge electrode is earthed. Means are therefore provided to charge the discharge electrode to a potential of polarity suitable to discharge the spray. All the droplets in the spray can be discharged without upsetting the formation of a ligament.

In one form, the invention provides an inhaler for producing a spray of droplets of a liquid to be inhaled, comprising: walls defining with a shield electrode, a chamber having an air passage therethrough; a spraying edge, the shield electrode being spaced from the edge and having an orifice through which liquid sprayed from the edge can issue into the chamber; means for producing a charge to a high potential of one polarity relative to the shield electrode in liquid at the spraying edge, to define an electric field between the edge and the shield electrode sufficient to cause the liquid to issue from the spraying edge as at least one cone from which electrostatic forces repel through the orifice a ligament which breaks up into a spray of charged droplets; a sharp discharge electrode spaced from the shield electrode in said chamber; means for charging the discharge electrode to a high potential of the other polarity relative to the shield electrode, such as to produce a corona to discharge the spray, the shield electrode being of sufficient overall dimensions and having a sufficiently small orifice to shield the edge and the cone of liquid from the corona.

Problems can arise when it is attempted to put the spraying edge, shield electrode and discharge electrodes inside a chamber. For example, there is a tendency for the spray to deposit on the chamber walls. There is more than one mechanism which may produce this effect. Obviously there may be some deposits due to collisions between the discharged droplets and the chamber walls. A much greater deposit may be caused, however, if the spray is not completely discharged due, for example to the voltage on the discharge electrode not being high enough or being poorly directed. Any droplets remaining charged will deposit on the chamber walls. To assist the discharge of the spray, the chamber is preferably swept completely by corona to the shield electrode, so that there are substantially no pockets where droplets could escape being discharged. To this end, the discharge electrode is preferably positioned at the chamber wall and protrudes into the chamber from the wall by a small amount. The chamber wall at which the discharge electrode is positioned is also preferably concave with respect to the chamber, so that there is little or none of the chamber behind the corona.

Droplets may also be caused to deposit on the chamber walls if the walls become charged by corona from the discharge electrode. This may be caused by the discharge electrode being at too high a voltage, so that there is spare corona after the spray has all been discharged, or by the discharge electrode being poorly directed or positioned. The walls become charged oppositely to the spray, which attracts both charged and discharged droplets. The walls may become so highly charged as to produce a reduction in the corona discharge from the discharge electrode. In turn that may cause less than all of the spray to be discharged.

This effect may be reduced or prevented by choosing a material for the chamber walls which is less than completely insulating so that if corona produces unwanted charge on the walls, this can leak away. Additionally or alternatively, the shield electrode may be cup shaped, inside or forming part of the chamber walls extending towards the discharge electrode.

BRIEF DESCRIPTION OF THE DRAWINGS

An embodiment of the invention, given by way of example, will now be described with reference to the accompanying drawing, in which:

FIG. 1 shows schematically and partly in section, an inhaler embodying the invention;

DETAILED DESCRIPTION

Figure 2:
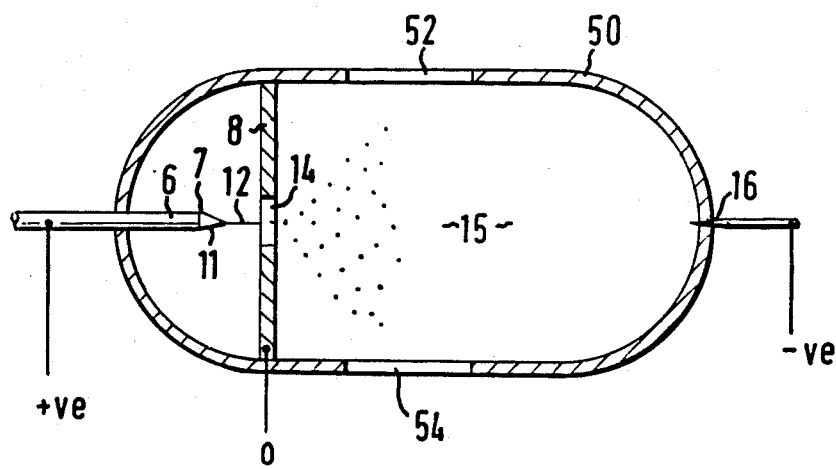
FIG. 2 shows an enlarged section of part of the apparatus of claim 1.

Referring to FIGS. 1 and 2 (which are not to scale), liquid which it is desired to atomise is supplied via an insulating pipe 2 to an outlet 6 for the liquid. In the apparatus illustrated the outlet 6 is a metal capillary tube and is thus electrically conducting. The end of the outlet provides a spraying edge from which the liquid is sprayed.

Spaced from and in front of the spraying edge 7 is a shield electrode 8. The outlet 6 and the shield electrode 8 are connected to respective terminals of a high voltage generator 10 which in use charges the spraying edge 7 to a high voltage of one polarity, preferably positive, with respect to the shield electrode 8. The voltage between the spraying edge 7 and the shield electrode 8 produces a sufficient electrode field strength between them to draw a cone 11 of liquid from the spraying edge. The liquid leaving the spraying edge becomes charged, negative charge being conducted away by the conducting spraying edge 7, leaving a net positive charge on the liquid. The charge on the liquid produces internal repulsive electrostatic forces which overcome the surface tension of the liquid forming a cone of liquid from the tip of which issues a ligament 12. At a distance from the spraying edge, the mechanical forces produced on the ligament due to travelling through the air cause it to break up into charged droplets of closely similar size. The shield electrode 8 replaces the field intensifying electrode described in the above mentioned British patent specification No. 1,569,707.

In order to produce the very small droplets necessary for an inhaler, the electric field strength produced between the spraying edge and the shield electrode needs to be high. For example, the voltage between the shield electrode 8 and the spraying edge may be in the region of 5 Kv, whilst the spacing between them may be less than 5 mm, say, 2 mm. It is known that air ionises differently at the different polarities and that the threshold is higher for positive potentials. In order to produce the small droplets referred to, the electric field strength is found to be so high that if the spraying edge 7 is charged negative relative to the shield electrode 8, there is a substantial risk of corona from the spraying edge and/or the cone 11 which interferes with or destroys the stability of the ligament. We have found that suitably small droplets can be produced when the spraying edge is charged positive, without the risk of corona from the spraying edge 7 or cone 11.

The formulations used in inhalers have a resistivity which is much lower than that usually used for electrostatic spraying. In most prior art applications, say, paint spraying or spraying agricultural pesticides, in order to obtain a useful flow rate, the liquids to be sprayed usually have resistivities in the range $10^6$ to $10^{10}$ ohm cm. The formulations which might be used in an inhaler are expected to have resistivities in the range $5 \times 10^3$ to $10^8$ ohm cm. Although spraying of liquids which have a resistivity at the low end of the range is known from, say, U.S. patent specification No. 1,958,406 it only works at low flow rates which have not been of much practical use. If the flow rate is too high, the ligament becomes unstable. We have found, however, that a stable ligament can be produced, and the apparatus can be made to spray satisfactorily, if the flow rate is low enough, a situation which is appropriate to inhalers, but not perhaps to agricultural or paint sprayers. It is likely that suitable formulations will have resistivities in the range $10^5$ to $10^7$ ohm cm. Given that a stable spray can be produced, the lower resistivities assist in the production of a small droplet size. All other parameters equal, we find that the lower the resistivity, the smaller the droplet size.

The shield electrode has an orifice 14 aligned with the spraying edge 7 and sufficiently large that the ligament or the droplets pass through, dependent on whether the ligament breaks up before or after the shield electrode, to produce a spray of droplets in a chamber 15 beyond the shield. If the orifice were too small the droplets or ligament would deposit on the shield electrode 8. Previous expectations as expressed in the above mentioned British patent specification No. 1,569,707 would have been that with the shield electrode positioned downstream of the atomising tip of the ligament, droplets would deposit on the shield electrode even with an orifice very substantially larger than illustrated. A small orifice is required in the present apparatus for reasons explained below.

In order to produce a spray which is inhalable, the droplets which issue through the orifice 14 must be discharged. This is effected by a discharge electrode in the form of a needle 16. In the embodiment illustrated, the needle is directly in the path of the spray. In alternative embodiments, one or more discharge electrodes may be positioned out of the direct path of the spray. The discharge electrode is connected to the high voltage generator 10 which, in use, charges the discharge electrode 16 to a high potential relative to the shield electrode 8 and of opposite polarity to that of the spraying edge, in this case negative. The shield electrode may be provided with a connection to earth, perhaps via a leakage path through the user of the inhaler, or may be left floating.

The discharge electrode 16 is driven to a sufficiently high voltage relative to the shield electrode 8 as to produce a corona discharge. The negative ions so produced discharge droplets in the spray issuing through the orifice 14.

The distinction between charged droplets and discharged droplets is very obvious visually. Any droplets remaining charged in the spray, are highly mobile in a predictable path. Discharged particles appear as a cloud or smoke which drifts unpredictably in the air currents.

If a prior art field intensifying electrode were used in the place of the present shield electrode, there would be considerable difficulty in discharging all the droplets in the spray. Why this is so can be understood by considering what happens as the voltage on the discharge electrode is increased from a voltage insufficient to cause ionic discharge.

Figure 4:
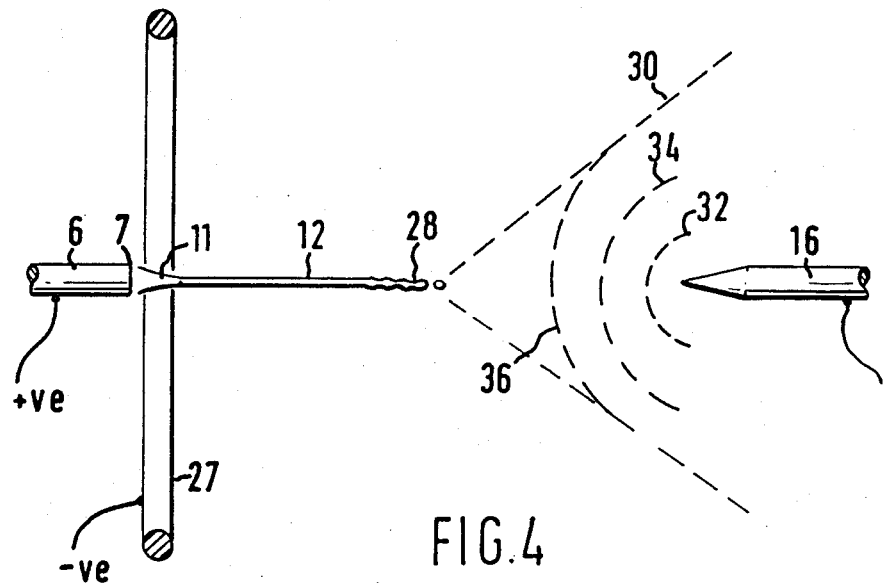
FIG. 4 illustrates schematically the effect of discharging the spray in a prior art electrode arrangement.

FIG. 4 shows an enlarged and schematic view of what would happen. A prior art field intensifying or field adjusting electrode is illustrated at 27. At the larger scale used in FIG. 4, the ligament 12 can be seen oscillating at 28 due to mechanical disturbance of passing through the air. The ligament breaks up into droplets which separate into a spray bounded approximately by a cone indicated in broken outline at 30. Within the spray, the charged droplets are highly mobile in predictable paths generally to the right of FIG. 4. At a threshold the voltage is sufficiently high that the electric field strength around the sharp tip of the needle ionises the surrounding air leaving free negative ions. These discharge surrounding droplets in an area bounded, say, by broken line 32. The discharged droplets are easily identifiable visually. They lose their predictable mobility, becoming a drifting smoke which is very distinct from the charged droplets. As the voltage is increased droplets are discharged further from the discharge electrode, so that more of the spray is discharged as indicated by, say, broken line 34. When the voltage applied to the needle is sufficiently high that the boundary of the discharged droplets, indicated by broken line 36, reaches the edge of the spray cone 30, the spray (which is travelling to the right in FIG. 3) would be completely discharged. Unfortunately, at this point the corona uncontrollably jumps to the cone 11 and/or the spraying edge 7, which discharges the cone 11. Since it was the charge on the liquid which overcame the surface tension thereof to form the cone 11 and repel the ligament 12 therefrom, discharging the cone 11 destroys the spray.

The shield electrode 8 is arranged to shield the spraying edge 7 and the cone 11 from the corona thus enabling all the droplets in the spray to be discharged without danger of the cone being discharged. To achieve this, the orifice 14 must not be too large otherwise corona will find its way through. As mentioned above, the orifice must not be too small either, otherwise the droplets will not spray through the orifice but will deposit on the shield electrode. We have found it entirely possible to balance these conflicting requirements so that the orifice can be at the same time neither too large nor too small. With a flow rate of about 40 microliters per minute, we found that the apparatus could be made to work with a hole 14 having a diameter in the range 2 mm to 1 cm. At the small end of the range, there was a greater tendency to spray onto the shield electrode. At the large end of the range, there was a greater tendency for the corona to leak through the hole to the cone 11. Complete discharge of the spray can be ensured by adjusting the position of the needle 16 and the voltage applied thereto. We found no need in the arrangement illustrated for the voltage to be more than 10 Kv and that it could, indeed, be well below that.

The overall dimensions of the shield electrode must be sufficient to prevent corona reaching the cone 11 or spraying edge 6 round the outside of the electrode.

The shield electrode 8 may be metallic but need not necessarily be of such a good conductor as that. What is required is that the shield electrode should be sufficiently conducting to remove any charge which may accumulate due to the ionic discharge.

The outlet 6, shield electrode 8 and discharge electrode 16 are contained within a capsule 50 having a volume of about 200 ml, defining the walls of the chamber 15. In order to reduce interference with the electrical fields produced between the spraying edge and the shield electrode on the one hand, and the discharge electrode and the shield electrode on the other hand, the capsule is made of an insulating or semi-insulating material. Polyethylene plastics is an example of a very highly insulating material. In order that any charge received by the capsule may leak away, it may be preferred to use a less insulating material for example polycarbonate, polyethylene terephthalate or polyacetal. The shield electrode may be cup shaped extending inside the walls towards the discharge electrode, or may form part of the walls.

Two holes 52 and 54 provide an air passage through the chamber 15 transverse to the direction in which the spraying edge sprays. The discharged spray can thus be removed in an airstream across the chamber and inhaled. The airstream may be produced by the user inhaling or, if necessary or preferred, by a fan (not shown).

The discharge electrode 16 has a sharp tip which just projects into the chamber 15. The wall containing the discharge electrode is concave with respect to the chamber. Both these features are intended to reduce the volume of the chamber which is behind (to the right in FIG. 2) of the corona discharge. It is desired that the corona discharge sweeps as much of the chamber 15 as possible without being so directed as to charge the walls of the chamber which would be both wasteful and could charge the walls so interfering with the formation of corona as mentioned above.

To facilitate the user inhaling the discharged spray, the air passage communicates with a face mask 36 as shown in FIG. 1. A non return valve, for example a flap (not shown), may be placed between the face mask and the capsule to prevent exhaled breath blowing the discharged droplets out through the hole 54.

Also shown in FIG. 1 is a supplies pack 38, which in this case is shown separate. The liquid supply tube 2 and the high voltage electrical leads are bundled together as indicated schematically. A mobile emphysema patient, for example, can put the supplies pack in a pocket and move about whilst using the mask. The supplies pack contains the high voltage generator 10 and delivery means 40 for supplying metered amounts of the liquid to be inhaled.

The flow rate of the liquid supplied to the outlet 6 is required to be very accurate. Accuracy is required both so that the patient gets the correct dose, and so that the droplet size remains accurate.

In order to achieve the required accurate flow rate, the delivery means 40 comprises a syringe 42 containing the liquid. The syringe is replaceable when empty. The syringe has a plunger 44, which is driven directly by a friction wheel 45. This is driven by a stepping motor and reduction gearbox 46 controlled by an electrical controller 48 which may include means for setting the rate, or alternatively the rate may be fixed. This general arrangement is already used in a metered pump for administering successive doses of insulin. The pump is manufactured by Muirhead Vactric Components Ltd. of Beckenham, Kent.

Although the outlet capillary tube 6 is metallic in the above example, it is possible to use an insulating tube, especially when the liquid to be atomised has a resistivity towards the lower end of the range. In this case an electrode contacts the liquid upstream of the spraying edge. The liquid is itself sufficiently conducting to carry the charge to the spraying edge so to define the electric field between the spraying edge and the shield electrode 8. The lower the resistivity of the liquid the further upstream contact can be made with the liquid.

Although illustrated as one integral piece the capsule 50 may be formed as two separable parts to facilitate cleaning.

Figure 3:
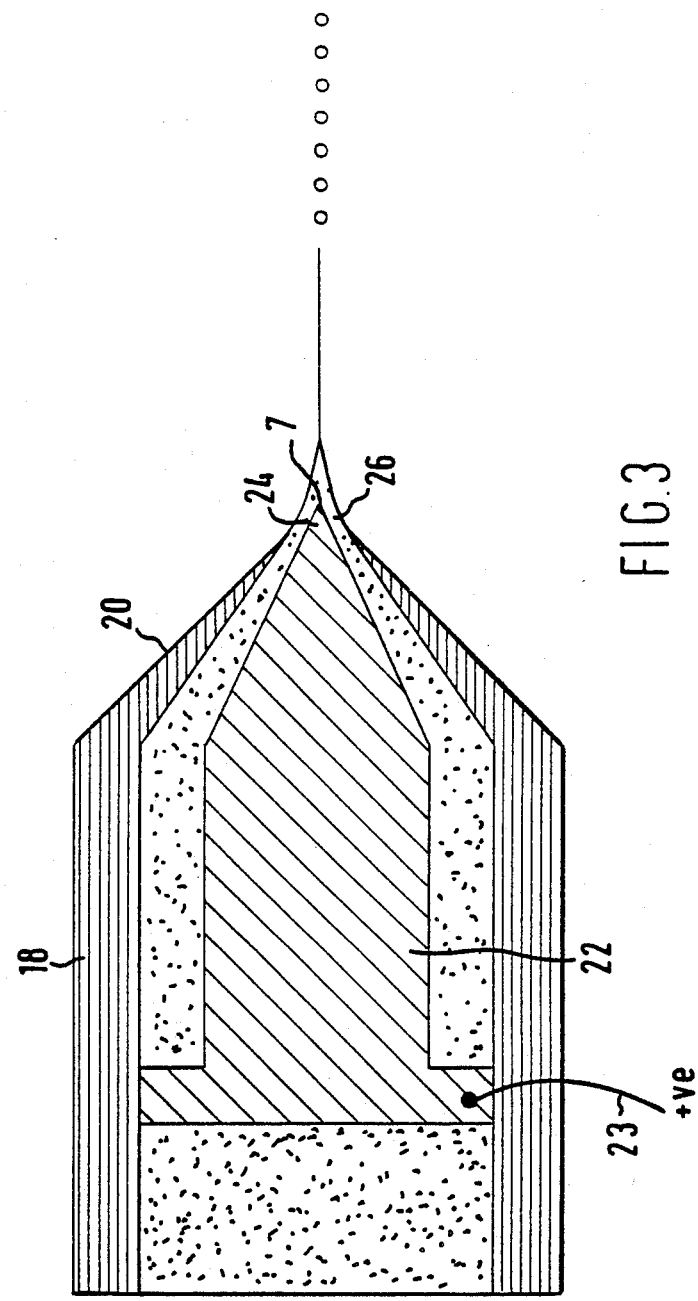
FIG. 3 is a schematic cross section through an alternative spraying edge 7 for the apparatus of FIG. 1.

A further form of spraying edge is illustrated in FIG. 3. This spraying edge comprises an outer insulating tube 18 tapered externally at one end 20. A conducting core 22 is connected to the high voltage generator 10 by a lead 23. The core 22 tapered to a point 24 at one end. The point 24 projects slightly beyond the outer insulating tube so defining an annular orifice 26 therewith. The arrangement produces a single ligament from the tip of the projecting point of the core.

All the examples of spraying edges described above are arranged to produce a single ligament principally because of the very low flow rate which may be required in the particular application of an inhaler. In applications where higher flow rates may be required, it may be appropriate to use a spraying edge which produces a plurality of ligaments. One form of spraying edge which produces a plurality of ligaments is a linear nozzle (not shown). In this form liquid is fed to a a linear edge at which the intense electric field is formed. The linear edge may be fed with liquid from a slot at or spaced from the edge. A linear nozzle is illustrated in British patent specification No. 1569707. If the edge is plane, ligaments from along its length at intervals determined by various factors including the field strength and the flow rate. It is possible to position the ligaments to some extent by means of irregularities in the edge, for example teeth, which provide local intensification of the field from which the ligaments issue.

To illustrate the use of a linear nozzle, FIG. 2 could still be considered a cross section through the apparatus, the outlet 6, shield electrode 8 and discharge electrode 16 all extending linearly at right angles to the plane of the paper. In effect the outlet would be a slot feeding a linear edge. It is possible to space the slot back from the edge, as would be the case if the arrangement of FIG. 3 were considered to be a section through a linear nozzle. The spraying edge would then be a linear edge instead of a point described above, and the annular orifice would be a slot above and below the edge. The edge could be fed from a slot on just one side. In such arrangements the orifice 14 in the shield electrode is in the form of a slot and the discharge electrode is either in the form of an edge or a row of discrete points as that illustrated.

Formulations suitable for use with an inhaler embodying the invention, are likely to have a resistivity in the range $5 \times 10^3$ to $10^8$ ohm cm.

Predominantly aqueous formulations are not completely satisfactory, since the droplet size is so small that evaporation takes place very quickly. Water also has a high surface tension which makes it difficult to spray. Suitably the formulation comprises an acceptable organic diluent and the amount of water, if present, comprises not more than about 50% of the total diluent, more suitably less than 20% and preferably less than 10%.

The formulation consists of a suitable, pharmaceutically acceptable, solvent e.g. dimethyl isosorbide, glycerol, propylene glycol and polyethylene glycol of average molecular weight up to about 600 admixed with water or ethanol. In addition the formulations may contain a suitable pharmaceutically acceptable surfactant e.g. polyethoxy-ethylated castor oils ("Cremophors"), polyoxyethylene-polyoxypropylene block copolymers ("Pluronics", "Synperonics"), polyoxyethylene sorbitan derivatives ("Tweens"), polyoxyethylene oleyl ethers ("Brijs") and sorbitan esters of fatty acids ("Spans"). Such materials are preferably present at not more than 1% concentration.

An inhaler embodying the invention is suitable for the administration to a patient of any drug which can be administered via the lungs, either to have a direct effect on the lungs, for example for the treatment of asthma, emphysema or bronchitis, or for absorption from the lung into the bloodstream in order to produce a systemic therapeutic effect elsewhere in the body. Examples of drugs which have a direct effect on the lung for the treatment of asthma, emphysema or bronchitis are bronchospasm relaxants such as adrenaline, isoprenaline, orciprenaline, ephedrine, phenylephrine, diphenhydramine, terbutalene, isoetharine, etafedrine, methoxyphenamine, theophylline, aminophylline, salbutamol, sodium cromoglycate, ipratropium bromide, beclomethasone, betamethasone valerate, fenoterol reproterol, pirbuterol, budesonide, ketotifen and compounds as defined and claimed in published European patent specification No. 189 305, particularly those compounds defined in claims 4, 5 and 6. Examples of drugs which can be administered systemically via the lungs include polypeptide drugs, for example luteinising hormone-releasing hormone, and synthetic analogues thereof.

Suitably the active ingredient is in the formulation in a concentration range of 0.1 to 20%, and preferably 5 to 10%, but the required concentration depends, naturally, upon the potency of the particular drug being used.

We claim:

1. Apparatus for producing a spray of droplets of a liquid, comprising: a spraying edge; means for supplying the liquid to the spraying edge; a shield electrode spaced from the spraying edge and having an orifice through which liquid sprayed from the edge can issue; means for producing a charge to a high potential of one polarity relative to the shield electrode in liquid at the spraying edge, to define an electric field between the edge and the shield electrode sufficient to cause the liquid to issue from the edge as at least one cone from which electrostatic forces repel through the orifice a ligament which breaks up into a spray of charged droplets; a sharp discharge electrode located on the other side of the shield electrode from the spraying edge and directed toward the orifice of the shield electrode; means for charging the discharge electrode to a high potential of the other polarity relative to the shield electrode, such as to produce a corona to discharge the spray, the shield electrode being of sufficient overall dimensions and having a sufficiently small orifice to shield the edge and the cone of liquid from the corona.

2. An inhaler for producing a spray of droplets of a liquid to be inhaled, comprising: a housing; a shield electrode mounted within said housing so as to define with the walls of said housing a chamber within the housing, said sheild electrode having an orifice defined therethrough; at least two apertures defined in said walls and spaced apart so as to define an air passage through the chamber so that droplets in the chamber can travel out of the chamber while air enters the chamber; a spraying edge; means for supplying a liquid to be sprayed to the spraying edge, said spraying edge directing sprayed liquid toward the orifice in the shield electrode, said spraying edge being spaced from said shield electrode and defined exteriorly of said chamber so that liquid sprayed from the spraying edge can issue into the chamber through said orifice in said shield electrode; means for producing a charge to a high potential of one polarity relative to the shield electrode in liquid at the spraying edge, to define an electric field between the spraying edge and the shield electrode sufficient to cause the liquid to issue from the spraying edge as at least one cone from which electrostatic forces repel through the orifice a ligament which breaks up into a spray of charged droplets; a sharp discharge electrode mounted within said chamber and spaced from the shield electrode, said sharp discharge electrode being defined on the opposite side of the shield electrode from the spraying edge; means for charging the discharge electrode to a high potential of an opposite polarity relative to the shield electrode, so as to produce a corona to discharge the spray, the shield electrode being of sufficient overall dimensions and having a sufficiently small orifice to define a means for shielding the edge and the cone of liquid from the corona.

3. An inhaler as claimed in claim 2, including a face mask and means connecting the face mask to one of said apertures.

4. An inhaler as claimed in claim 2, wherein the discharge electrode is positioned at the chamber wall opposite the spraying edge and protrudes into the chamber from the wall by a small amount, the chamber wall being insulating or semi-insulating at least in the vicinity of the discharge electrode.

5. An inhaler as claimed in claim 4, wherein the chamber wall at which the discharge electrode is positioned is concave with respect to the chamber.

6. An inhaler as claimed in claim 4, wherein the air passage is transverse to the direction of spray.

7. An inhaler as claimed in claim 2, further comprising means on the spraying edge to produce a spray having a droplet size of from 2 to 5 microns diameter when used with a liquid having a resistivity in the range from $5\times10^3$ ohm cm. to $10^8$ ohm cm.

8. An inhaler as claimed in claim 7, wherein the liquid sprayed from the spraying edge has a resistivity in the range from $10^5$ to $10^7$ ohm cm.

9. An inhaler as claimed in claim 2, wherein the spraying edge includes means to produce a single ligament.

10. An inhaler as claimed in claim 9, wherein the spraying edge comprises an annular orifice arranged to feed liquid to the surface of a pointed core extending from the annular orifice toward the chamber, so that, in use, the single ligament issues from the point of the core.

11. An inhaler as claimed in claim 10, wherein the spraying edge comprises the end of a capillary tube.

12. An inhaler as claimed in claim 2, wherein the means for charging the liquid is arranged to charge the liquid to a positive potential relative to the shield electrode.

* * * * *